United States Patent [19]

Updegrave

[11] 4,048,506
[45] Sept. 13, 1977

[54] VERSATILE INTRAORAL RADIOGRAPHIC FILM POSITIONING SYSTEM

[76] Inventor: William J. Updegrave, Riverbend Apt. 603, 3010 N.E. 16th Ave., Ft. Lauderdale, Fla. 33334

[21] Appl. No.: 647,732

[22] Filed: Jan. 9, 1976

Related U.S. Application Data

[63] Continuation-in-part of Ser. No. 542,073, Jan. 17, 1975, abandoned.

[51] Int. Cl.² ............................................. G03B 41/16
[52] U.S. Cl. ..................................... 250/479; 250/521
[58] Field of Search ................ 250/478, 479, 475, 521

[56] References Cited

U.S. PATENT DOCUMENTS

| 1,923,669 | 8/1933 | Harrison | 250/479 |
| 2,090,933 | 8/1937 | Bolin | 250/521 |
| 2,245,395 | 6/1941 | Goldberg | 250/521 |
| 2,688,096 | 8/1954 | Galliano et al. | 250/521 |
| 3,304,422 | 2/1967 | Medwedeff | 250/479 |
| 3,473,026 | 10/1969 | Updegrave | 250/479 |
| R. 25,773 | 5/1965 | Medwedeff et al. | 250/521 |

Primary Examiner—Alfred E. Smith
Assistant Examiner—B. C. Anderson
Attorney, Agent, or Firm—Woodcock, Washburn, Kurtz & Mackiewicz

[57] ABSTRACT

A universal intraoral radiographic system for taking periapical as well as bite-wing radiographs comprises a bite block, a bite block holder and an x-ray beam alignment means. The bite block includes a bite portion having a substantially vertically extending film-holding slot permitting the film to extend therethrough into any desired position. A film-locking slot extends substantially horizontally through the bite portion so as to receive the bite block holder which locks the film in place within the film-holding slot. The x-ray beam alignment means or target comprises a substantially planar piece of radio transparent material which may have circular indicia for aligning an x-ray beam of circular cross-section or rectangular indicia for aligning an x-ray beam of rectangular cross-section. The system may also be used to practice the occlusal technique by utilizing an occlusal film holder having a coupling portion adapted to be received by the film-holding slot.

44 Claims, 20 Drawing Figures

_Fig. 11_

_Fig. 12_

VERSATILE INTRAORAL RADIOGRAPHIC FILM POSITIONING SYSTEM

RELATED APPLICATION

This application is a continuation-in-part of application Ser. No. 542,073 filed Jan. 17, 1975 now abandoned.

BACKGROUND OF THE INVENTION

This invention relates to radiography, and more particularly, to dental or intraoral radiography. In dental radiography, one of the principal techniques utilized for producing radiographs of teeth is referred to as the paralleling or right angle technique. The paralleling technique encompasses radiographs which are taken in the periapical position (both maxillary and mandibular) as well as radiographs which are taken in the bite-wing position. Another useful technique for taking radiographs is the occlusal technique which practices the rule of isometry.

Heretofore, radiographs which have been taken in the periapical position have necessitated the use of different radiographic instrumentation than that utilized for radiographs taken in the bite-wing position. For example, radiographic instrumentation including a particular film-holding bite block for taking radiographs in the periapical position (both maxillary and mandibular) are disclosed in my patent application Ser. No. 581,237 filed Sept. 22, 1966 (now abandoned) and my U.S. Pat. No. 3,745,344. Instrumentation including a different film-holding bite block for radiographs taken in the bite-wing position is disclosed in my application Ser. No. 581,048 filed Sept. 21, 1966 (now abandoned). Instrumentation utilized in practicing the rule of isometry or the bisecting angle technique are shown in my U.S. Pat. No. 3,473,026 as well as U.S. Pat. No. 1,923,669 — Harrison.

It will therefore be understood that different instrumentation is required depending upon whether the radiographs are being taken in the periapical, the bite-wing, or bisecting angle position. In this connection, it may be noted that the bite blocks used in the periapical position as well as the bite-wing position comprise a groove which only allows the radiographic film to be placed in a single position in the bite block. U.S. Pat. No. 2,240,336—Kreider does disclose a bite block which is utilized to hold films in the bite-wing position but also includes a slot which does allow the radiographic film to be positioned in a perapical position. However, the film is prone to move in the slot and is particularly difficult to maintain in the periapical position where only an edge of the film is received in the slot.

Of course, even if the radiographic film could be positioned in both the periapical and bite-wing position within a single bite block, it would still be necessary to move the x-ray beam with respect to that bite block so as to assure proper coverage of the radiographic film by the beam. In this connection, various alignment assisting mechanisms have been utilized including linear rods and alignment frames which may be circular when a circular beam is utilized as disclosed in the aforesaid abandoned applications and by U.S. Pat. No. 3,743,026 as well as a rectangular frame as disclosed in my U.S. Pat. No. 3,745,344. However, these alignment mechanisms would be ineffective to properly direct the x-ray beam for both periapical and bite-wing positions of the radiographic film. Moreover, these alignment mechanisms require a fair degree of training and experience to properly utilize. However, with the increased demands on the time of dentists, it is often desirable to leave the radiography to dental hygienists or assistants, some of which may be lacking in experience.

SUMMARY OF THE INVENTION

It is an overall object of this invention to provide a novel intraoral radiographic instrumentation which, regardless of the experience or skill of the user, is capable of accurately achieving alignment of the radiographic film, the teeth and the x-ray beam in a simplified and standardized manner such that radiographs can be accurately duplicated at future intraoral examinations for the purpose of checking the status of health of the teeth and supporting structures as well as the response of the tissues to therapy and home care regardless of the experience of the individual utilizing the instrumentation.

It is a more specific object of this invention to provide intraoral radiographic instrumentation which is capable of taking radiographs in the periapical as well as the bite-wing positions.

In accordance with these and other objects of the invention, a preferred embodiment comprises a bite block having a bite portion with an upper bite surface and a lower bite surface, a film-holding slot extending substantially vertically through the bite block at one end of the upper and lower surfaces so as to permit a film to extend into the slot and a film-locking slot extending substantially horizontally through the bite portion between the upper surface and the lower surface and in communication with the film-holding slot.

A bite block holder means associated with the bite block includes a film-locking portion in one end thereof. The film-locking portion is adapted to be removably received by the film-locking slot and engages the film thereby holding the film in a substantially fixed position within the film-holding slot.

An x-ray beam alignment or target means coupled to the bite block holder means assists in the alignment of the x-ray beam with the film in the film-holding slot.

In accordance with one important aspect of the invention, the locking portion comprises a roughened or serrated surface adapted to engage the film in the area of communication between the film-holding slot and the film-locking slot. This assures that the film is retained in the proper position within the slot whether that position is periapical or bite-wing. Moreover, the locking portion may be tapered and the film-locking slot may also be tapered in a similar or complementary manner such that the film-locking portion is wedged against the film. In addition, the film-holding slot may include a depression or two raised portions in the opposite side of the film-locking slot such that the film may be forced into the depression or between the raised portions by the film-locking portion thereby further assuring that the film is locked or held in the proper periapical or bite-wing position. Preferably, the bite portion is sufficiently flexible so as to assist in clamping the film-locking slot closed on the film-locking portion in response to pressure of the teeth on the upper bite surface and the lower bite surface.

In accordance with another important aspect of the invention, the x-ray beam alignment means comprises positioning means for indicating the mandibular periapical, the maxillary periapical and the bite-wing positions for the x-ray beam.

In accordance with yet another important aspect of the invention, the x-ray beam alignment means comprises radio transparent material having a substantially planar surface which is adapted to be juxtaposed to the end of an x-ray beam shaping means. Preferably, color coding designates the maxillary, mandibular and bite-wing positions on the planar surface to assist in aligning the x-ray beam with the film regardless of position.

In one embodiment of the invention, the x-ray beam shaping means comprises a circular tube. In another embodiment of the invention, the x-ray beam shaping means comprises a cap including a rectangular orifice which covers the end of a circular tube so as to generate a beam of rectangular cross-section. It will of course be understood that such a beam is particularly advantageous in reducing the amount of radiation to which a patient is exposed.

In the embodiment wherein the cap is applied to the circular tube for generating a beam of rectangular cross-section, the x-ray beam alignment means may also be color coded so as to assist in properly positioning the rectangular beam to assure the proper coverage of the film by the x-rays depending upon whether the film is placed in the horizontal or vertical position.

It is another object of this invention to provide intraoral radiographic instrumentation which is also capable of taking radiographs in the occlusal position.

In accordance with this object of the invention, the occlusal film support means comprises a coupling portion adapted to be received by the film-holding slot of the bite block and a film backing portion adapted to support the film. The coupling portion forms an obtuse angle with the film backing portion so as to support the film in the occlusal position.

DETAILED DESCRIPTION OF THE PARTICULAR EMBODIMENTS

Figures 1, 2, 3, 3A:
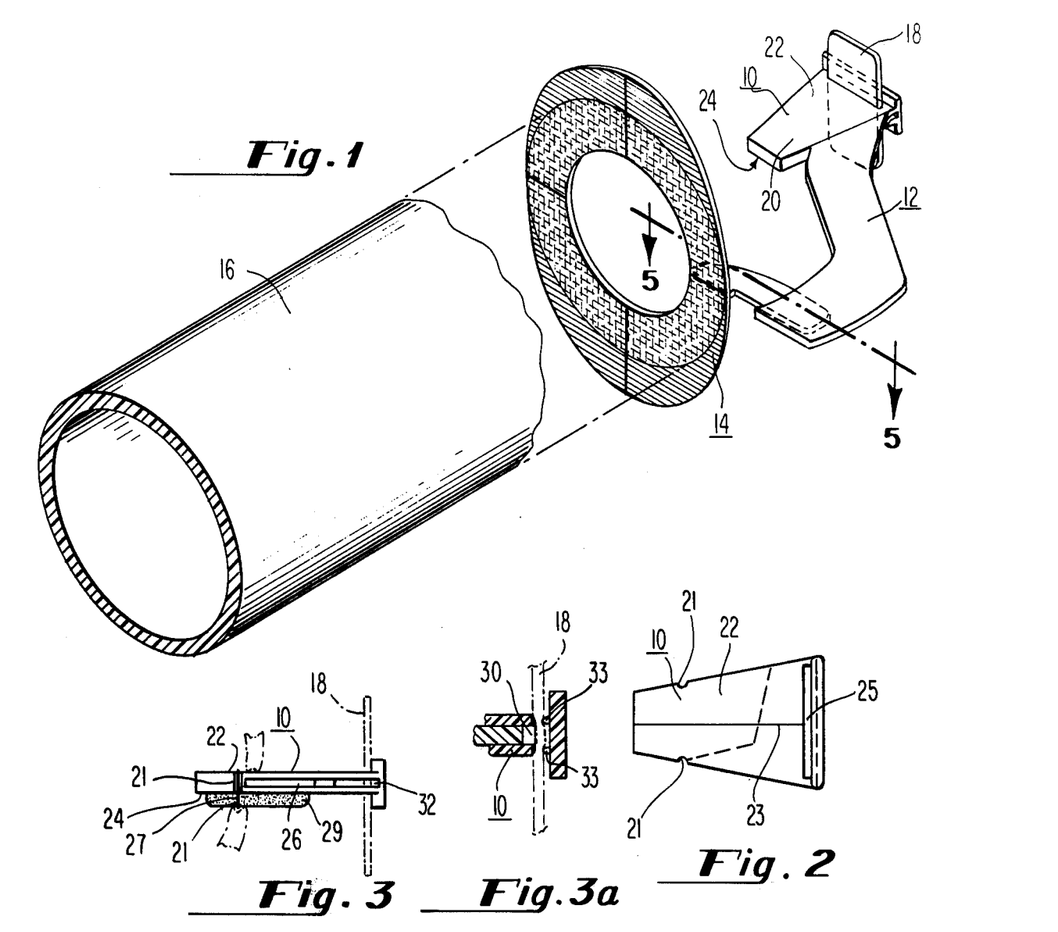
FIG. 1 is a perspective view of a preferred embodiment of the versatile intraoral positioning radiographic system of this invention.
FIG. 2 is a top view of the bite block shown in FIG. 1.
FIG. 3 is a side view of the bite block shown in FIG. 2.
FIG. 3a is a partial sectional view of the interaction between the bite block and holder in a slightly modified apparatus.

As shown in FIG. 1, the universal intraoral radiographic system of this invention comprises a bite block 10 which is removably attached to a bite block holder means 12 which also carries an x-ray beam alignment means 14 a fixed distance from the block 10. The x-ray beam alignment means 14 is adapted to be coupled to an x-ray beam shaping means or tube 16 which is radio opaque and attached to a suitable source of x-rays. As shown in the embodiment of FIG. 1, the tube 16 is circular and the x-ray alignment or target means 14 comprises circular or partially circular indicia to assist in aligning the x-ray beam with the alignment means and ultimately to the film 18 which is retained by the bite block 10.

The bite block 10 includes a bite portion 20 having an upper bite surface 22 and a lower bite surface 24 as shown in FIGS. 2 and 3. A film-holding slot 25 shown in FIG. 2 extends substantially vertically through the bite block at one end of the upper and lower bite surfaces 22 and 24 so as to permit the film 18 to extend through the slot from a position above the upper bite surface 22 to a position below the lower bite surface 24 as shown in FIG. 1. A center line 23 which is utilized to assist in visually positioning the bite block intersects the center of the film 18 and slot 25 at right angles thereby indicating the center line of the film.

In addition, the bite block 10 includes a film-locking slot 26 which extends substantially horizontally through the bite portion between the upper bite surface 22 and the lower bite surface 24.

Figure 4A:
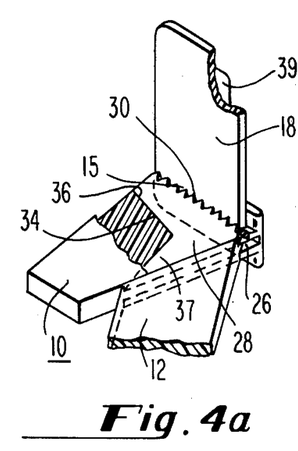
FIG. 4a is a fragmentary perspective of a film locked in place in the bite block of FIG. 1 in the maxillary periapical position.

As shown in FIG. 4a, the film-holding slot 25 communicates with the film-locking slot 26 so as to permit the film-locking portion 28 of the bite block holder means 12 to engage the film 18 within the film-holding slot 25. In this connection, the film-locking portion 28 includes a roughened or serrated edge 30 which provides a good deal of friction between the film-locking portion 28 and the film 18 to assure the proper positioning of the film 18 within the slot 25. In this same connection, it will be noted that the side of the film-holding slot 25 opposite the film-locking slot 26 is irregular and that it includes a depression 32 as shown in FIG. 3 which actually receives the deflected film 18 when the serrated edge 30 of the film-locking portion 28 is wedged into place to hold the film 18 in the proper position. As shown in the slightly modified embodiment of FIG. 3a, a depression is formed between ridges or beads 33 to receive the film when the serrated edge 30 of the film-locking portion 28 is wedged against the film.

The above-referenced wedging action is in part accomplished by providing the locking portion 28 with a tapering edge 34 which cooperates with a tapered surface 36 in the film-locking slot 26. As the locking portion 28 is then moved into the slot 26, the edge 34 is guided by the surface 36 so as to move the serrated edge 30 over and toward the film 18. Note that the locking portion 28 extends away from the film 18 within the slot 26 at section 37 so as to add stability and rigidity to the connection between the bite block holder 12 and the bite block 10.

Note the slot 25 and associated locking mechanism is capable of receiving single or double pack films and films having other variations in size, shape and thickness, e.g., films for use in child radiography as well as adult radiography. As shown in FIG. 3, grooves or recesses 21 may receive an elastic band 27 which attaches a stabilizing block 29 which may comprise a firm but compressible material, such as styrafoam, at the lower bite surface 24 so as to compensate for irregularities in opposing teeth shown in broken lines thereby stabilizing the bite block 10.

In accordance with another important aspect of the invention, the portions of the bite block 10 which are located between the film-locking slot 26 and the upper and lower bite surfaces 20 and 22 are sufficiently flexible so that the pressure of the teeth on the upper and lower surfaces 20 and 22 actually clamps the film-locking portion 28 in place within the film-locking slot 26. This provides double assurance that the film 18 within the film-holding slot 25 is incapable of moving from its preselected position. It may also be desirable to place a thin planar piece of material 39 behind the film 18 in the slot 26 to provide additional support for the film, thereby preventing distortion in a radiographic image incident to film curvature. The dimensions of the piece 39 may vary but are generally smaller than the dimensions of the film 18.

Figure 4B:
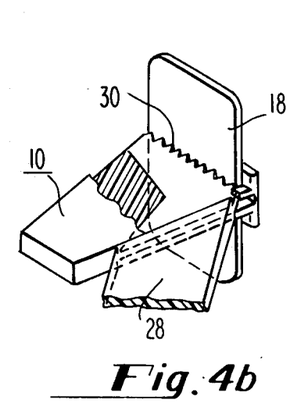
FIG. 4b is a fragmentary perspective view of a film locked in the bite block of FIG. 1 in the bite-wing position.
Figure 4C:
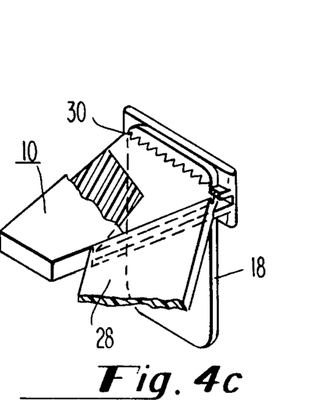
FIG. 4c is a fragmentary perspective of a film locked in the bite block of FIG. 1 in the mandibular periapical position.

As shown in FIG. 4a, the film 18 is in the maxillary periapical position with a substantial portion of the film 18 being located above the upper bite surface 20. However, by merely removing the film-locking portion 28 from the film-locking slot 26, the film 18 can be moved to the bite-wing position shown in FIG. 4b or the mandibular periapical position shown in FIG. 4c. Moreover, the film 18 may be maintained within the position shown in FIGS. 4b and 4c by merely reinserting the film-locking portion 28 in the film-locking slot 26 such that the serrated edge 30 engages the film 18 locking it into place.

Figure 5:
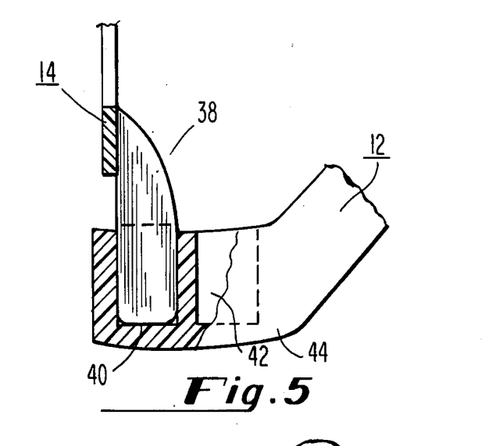
FIG. 5 is a sectional view taken along line 5—5 of FIG. 1.

As shown in FIG. 1, the beam alignment means 14 is carried by the bite block holder 12 at one end thereof. This is accomplished by providing the film alignment means 14 with an arm 38 which extends into one of the two slots 40 and 42 which extend horizontally through the end 44 of the bite block holder 12. As shown in FIG. 5, the arm 38 is inserted in the slot 40 closest to the end of the bite block holder 12. This position for the arm 38 of the beam alignment means is required where the patient's face is rather wide and posterior radiographs are being taken thereby necessitating the maximum space between the film 18 and the beam alignment means 14 as shown in FIG. 1. Where the patient's head is not that wide or where anterior radiographs are being taken, the slot 42 may be utilized to receive the arm 38.

The beam alignment means 14 will now be described in somewhat more detail with respect to FIG. 6. As shown there, the beam alignment function is performed by a piece of substantially radio transparent material having a planar surface 46 adapted to be juxtaposed to the end of a circular tube such as that shown in FIG. 1. The planar surface 46 carries color coded position designations to assist in properly aligning the circular x-ray beam shaping means or tube 16 with the film for the maxillary periapical, the mandibular periapical and the bite-wing positions. In the preferred embodiment of the invention, the color coding takes the form of a circular yellow band 48 at the center of the surface 46 and partially circular blue regions 50 and 52 located above and below the bands 48. When the tube 16 of FIG. 1 is aligned with the yellow band 48, the x-ray beam is in the proper position for taking bite-wing radiographs. When the circular tube 16 is aligned in part with the edge of the blue regions 50 and 52, the x-ray beam is in the proper position for taking maxillary periapical radiographs and mandibular periapical radiographs respectively.

It will be noted that proper x-ray beam alignment is achieved substantially entirely by the means 14. That is to say there is no use of an alignment rod which extends parallel with the axis of the x-ray beam and perpendicular to the film 18. In this connection, it has been found that the color coding is of great assistance in properly locating the circular tube 16 in the proper periapical or bite-wing position. At the same time, the planar surface 46 provides a relatively large surface area. This large surface area is very helpful visually in determining if the end of the circular tube 16 is substantially flush with the alignment means thereby assuring the proper angulation of the x-ray beam with respect to the film 18. For this purpose, the surface area of the surface 46 should be at least equal to 20% of the cross-sectional area of the x-ray beam. Note that the actual surface area is reduced by the presence of a circular opening 54 in the center of the surface 46. The opening 54 is provided so as not to block the dentist's or technician's view of the film by the alignment means 14.

Figure 7:
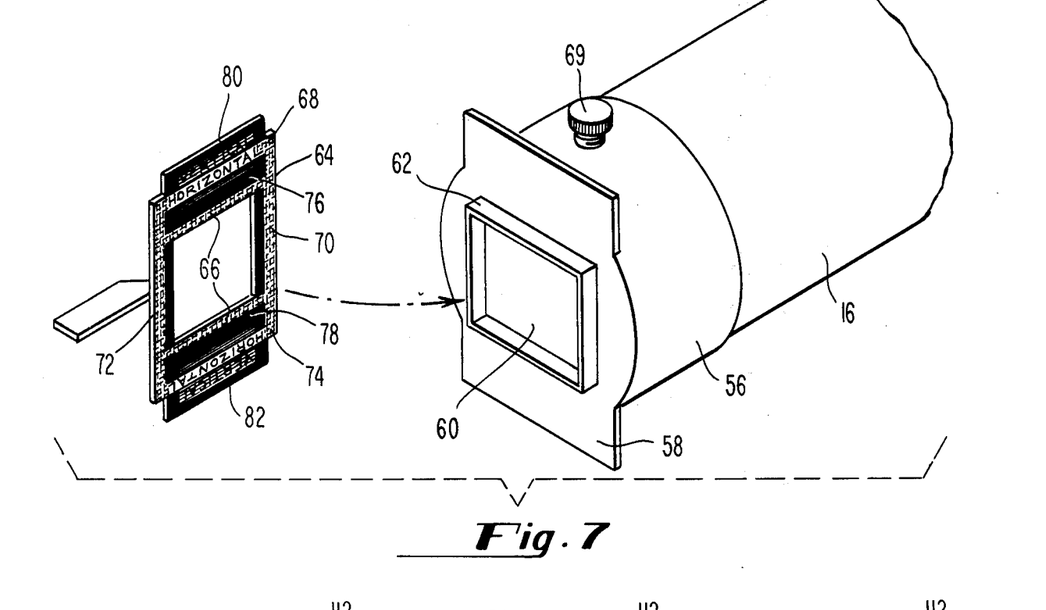
FIG. 7 is a perspective view of a rectangular beam alignment means and x-ray beam shaping means which may be utilized with the universal intraoral radiographic system of this invention.

FIG. 7 discloses another embodiment of the invention wherein a cap 56 is placed on the circular tube 16 so as to generate a beam of rectangular cross-section. For this purpose, the cap 56 comprises an end 58 of substantially radio opaque material having a rectangular orifice 60. The orifice 60 is surrounded by a rectangular frame 62 which is adapted to be aligned with color coded frames on a rectangular alignment means 64. With the rectangular orifice 60 in the horizontal position as shown in FIG. 7, the frame 62 would be aligned with the central yellow bars 66 and the vertical yellow bars 70 and 72 for taking bite-wing radiographs. In order to take maxillary periapical radiographs, the frame 62 would be aligned with the yellow bar 68 and the vertically extending yellow bars 70 and 72. In order to take mandibular periapical radiographs, rectangular frame 62 would be aligned with a lower yellow horizontal bar 74 and the vertical yellow bars 70 and 72. This horizontal position would be required for taking posterior radiographs wherein the x-ray film is generally placed in the horizontal position.

Where the film is placed in a vertical position for anterior radiographs, the cap 56 may be rotated by loosening the set screw 69 such that the orifice 60 is in the generally vertical position. Once in the generally vertical position, the frame 62 is aligned with the vertical frames formed by the black bars 76, 78, 80 and 82 for the bite-wing and periapical positions. Note that the surface of the alignment means 64 does comprise a substantial area, i.e., the area is at least 20% of the cross-sectional area of the rectangular beam. Of course, the means 64 includes the arm 38 for mounting on the bite block holder 12 not shown in FIG. 7.

Figure 8:
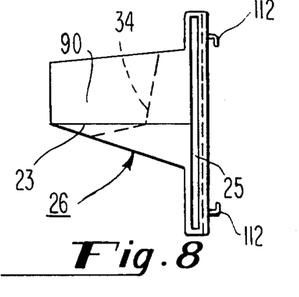
FIGS. 8–10 are top views of other bite blocks which may be utilized with the universal intraoral radiographic system of this invention.

While an anterior instrument has been disclosed in the embodiment of FIGS. 1, 2, 3 and 4(a-c), the invention is clearly not limited to that particular anterior instrument. In this connection, FIG. 8 shows a bite block 90 of a shape to permit its use in taking posterior radiographs. It will however, be understood that the various features of the bite block 10 shown in FIG. 1 are present in the bite block 90. For example, there is a film-holding slot 25 and a film-locking slot 26 having a tapering surface 34.

Figure 9:
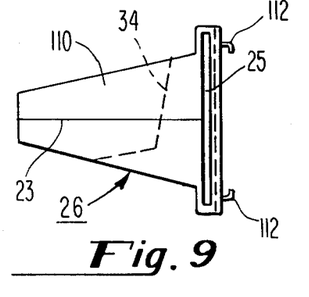
Figure 10:
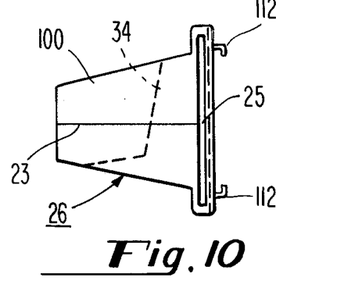

Another posterior bite block for taking posterior bite-wing radiographs with the film positioned vertically instead of in the conventional horizontal position is shown in FIG. 10. This permits greater coronal and alveolar bone crest coverage so essential in advanced periodontal disease. Again the features present in the bite block 10 are present in the bite block 100 of FIG. 10. Finally, FIG. 9 discloses another anterior bite block 110 having the same features as the anterior bite block 10 of FIG. 10 except that the slot 25 can accommodate a wider film.

All of the bite blocks may include line 23 on the bite surfaces thereof which is perpendicular to and intersects the film at the center thereof. They may also include ears 112 which are adapted to receive the plastic backing or support member 39 for the film 18. Note that placing the member 39 between the ears 112 and behind the slot 25 leaves the film free to interact with the groove 32 or ridges 33 as shown in FIG. 3a thereby assuring the film is locked in place.

Figure 11:
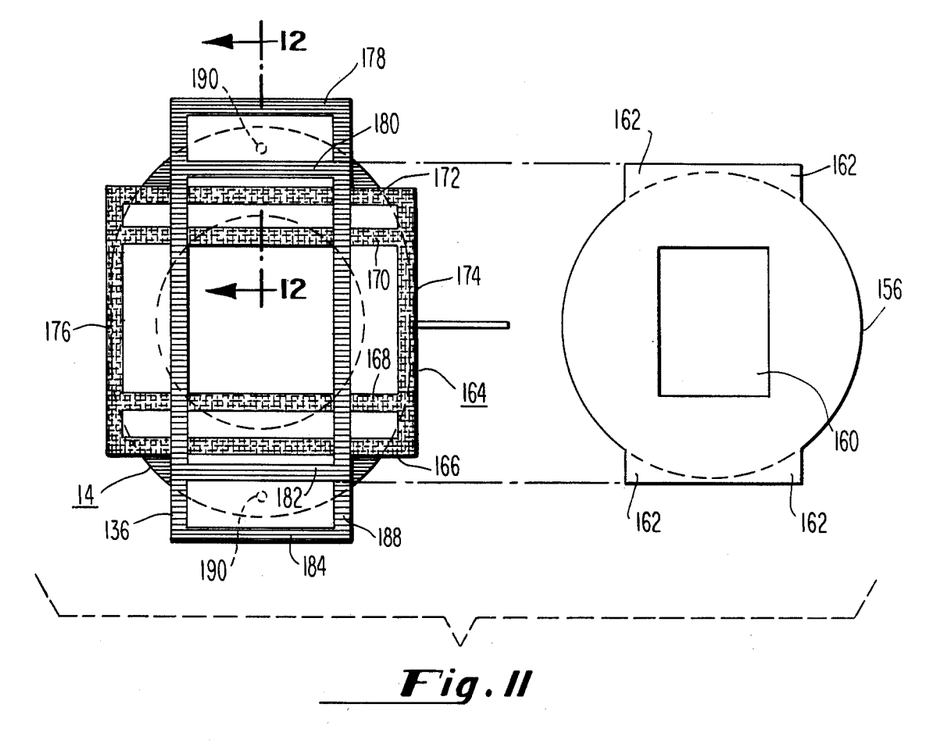
FIG. 11 is a perspective view of another rectangular beam alignment means and x-ray beam shaping means which may be utilized with the universal intraoral radiographic system of this invention.

A somewhat modified beam alignment means and rectangular beam shaping means is shown in FIG. 11. The beam shaping means comprises a cap 156 which is similar to the cap 56 shown in FIG. 7 except that the rectangular frame 52 has been eliminated thereby permitting the rectangular beam alignment means 164 to be placed flush against the surface of the cap 156 at the rectangular orifice 160. The cap 156 includes projections 162 which extend radially outwardly beyond the periphery of the circular tube on which the cap 156 is mounted.

Note that the projections 162 at least partially form a generally rectangular outline which is adapted to be juxtaposed to corresponding indicia on the beam alignment means 164. More particularly, the beam alignment means 164 includes indicia comprising horizontal rectangular outlines color coded in yellow which are formed by horizontal lines 166, 168, 170 and 172 as well as vertical lines 174 and 176. In addition, color coded indicia comprise blue horizontal lines 178, 180, 182 and 184 as well as blue vertical lines 186 and 188.

When the rectangular orifice 160 is oriented in the position shown in FIG. 11, i.e., the vertical position, the rectangular outline of the projections 162 is aligned with the various blue color coded lines. Of course, the particular horizontal lines 178, 180, 182 and 184 with which the rectangular outline formed by the projections 162 is aligned depends upon whether the radiograph being taken is a maxillary periapical, a bite-wing or a mandibular periapical. By rotating the cap 156 such that the rectangular orifice 160 extends generally horizontally, the rectangular outline of the projections 162 is aligned with the appropriate yellow color coded lines. Again, alignment with the horizontal yellow lines 166, 168, 170 and 172 depends upon the particular type of radiograph being taken, i.e., maxillary periapical, bite-wing or mandibular periapical.

Figure 6:
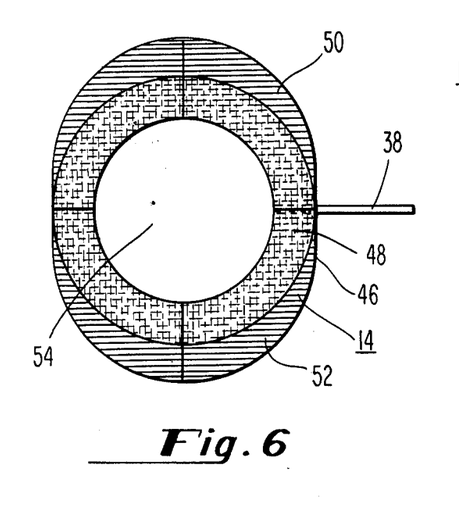
FIG. 6 is a plan view of the beam alignment means of FIG. 1.
Figure 12:
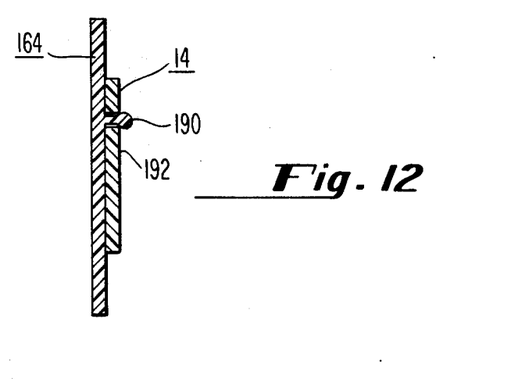
FIG. 12 is a partial sectional view of the rectangular beam alignment means cooperating with the circular beam alignment means.

It will be noted in FIG. 11 that the rectangular beam alignment means 164 is mounted on the circular beam alignment means 14 shown in FIG. 6. This is done as a matter of convenience and readily facilitates changeover from circular to rectangular beam, either by use of the beam shaping cap 56 or a rectangular collimating tube. The rectangular beam alignment means 164 is conveniently held in place by providing detents 190 which are received by small holes 192 in a circular beam alignment means 14 shown in FIG. 12. It will of course be appreciated that detents 190 permit the rectangular beam alignment means 164 to be snapped in place on the circular beam alignment means 14 with very little effort.

Figure 13:
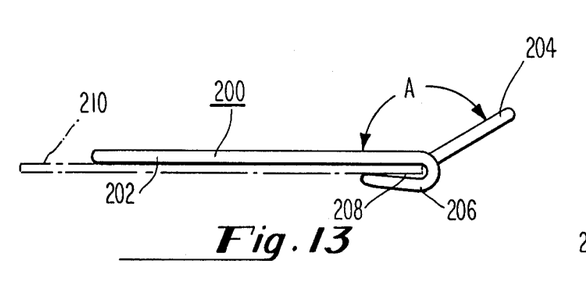
FIG. 13 is a side view of an occlusal film holder which may be utilized with the universal intraoral radiographic system of this invention.
Figure 14:
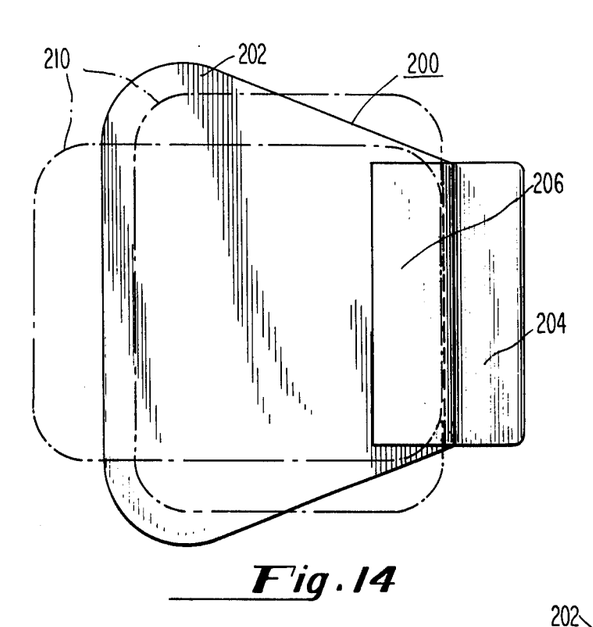
FIG. 14 is a bottom view of the occlusal film holder of FIG. 13.
Figure 15:
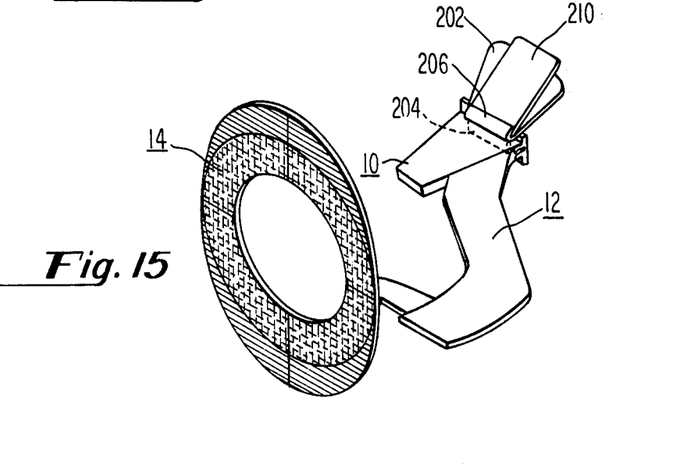
FIG. 15 is a perspective view of the intraoral radiographic system of this invention utilizing the occlusal film holder of FIGS. 13 and 14.

FIGS. 13 and 14 show occlusal film holder for use with the intraoral radiographic system shown in FIG. 15. The occlusal film holder 200 comprises a film backing portion 202 and a film coupling portion 204 extending away from the film backing portion at an obtuse angle A, e.g., 135°–165° and preferably 120°. A groove forming portion 206 is attached to the film holder 200 at the junction of the film backing portion and the film coupling portion 204 so as to form a groove 208 which is adapted to receive a film 210. As shown in FIG. 14, the film backing portion 202 is of a sufficiently large area so as to adequately support the film 210 in both the vertical and horizontal positions as depicted by the dotted lines.

Figure 16:
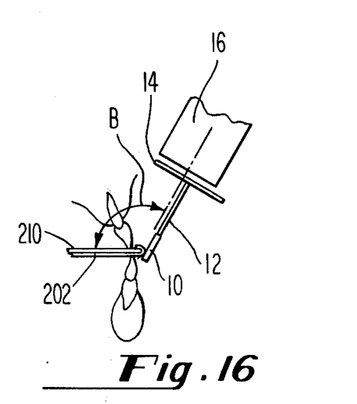
FIG. 16 is a sectional view of the intraoral radiographic system of this invention being utilized to take upper occlusal radiographs.
Figure 17:
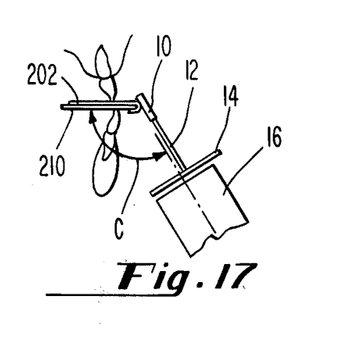
FIG. 17 is a sectional view of the intraoral radiographic system of this invention being utilized to take lower occlusal radiographs.

When the occlusal film holder 200 is utilized in conjunction with the bite block 10 and the bite block holder 12, the serrated edge 30 of the film locking portion 28 on the holder 12 engages the coupling portion 204 so as to firmly lock the coupling portion 204 of the film holder 200 in place. Insertion of the coupling portion 204 into the film locking slot 25 of the bite block 10 at the upper bite surface 22 allows the film 210 to be in contact with the incisal edges of the upper teeth as shown in FIG. 16. Similarly, insertion of the coupling portion 204 into the film-holding slot 25 from the lower bite surface 24 allows the film 210 to be in contact with the incisal edges of the lower teeth as shown in FIG. 17. In both instances, the film 210 and the film backing portion 202 form an angle B or C in the range of 105°–135° and preferably 120° with the axis of the x-ray beam, the upper and lower bite surfaces 22 and 24 and the plane of the holder 12. The angle formed between the plane of the alignment means 14 and the film backing portion 202 is in the range of 15°–45° and preferably 45°.

In both the upper and lower occlusal positions, the beam alignment means 14 serves to accurately align the x-ray beam so as to assure that the beam is properly directed at the film 210 to assure x-ray beam coverage of the film. In addition, the beam alignment means 14 assures proper practice of the rule of isometry which requires that the x-ray beam be directed perpendicularly to the imaginary plane which bisects the angle formed by the film surface with the long axes of the teeth being radiographed as shown in FIGS. 16 and 17.

The bite block, the bite block holder and the beam alignment means may comprise a variety of radio transparent materials. In addition to the radio transparent materials. In addition to the radio transparent quality, the plastic material must be non-toxic and have a sufficient rigidity to perform the various functions described in the foregoing. In this connection, material sold by E. I. DuPont de Nemours & Co., Inc. under the name of Delrin, has been found to be particularly suitable. Of course other materials having the same characteristics may be utilized including Lexan sold by General Electric Company.

Although specific embodiments of the invention have been shown and described, it will be understood that various modifications may be made without departing from the true spirit and scope of the invention as set forth in the appended claims.

What is claimed is:

1. Apparatus for positioning dental x-ray film within the mouth comprising:
   a bite block having a bite portion with an upper bite surface and a lower bite surface, a film-holding slot extending substantially vertically through said bite block at one end of said upper and lower surfaces so as to permit a film to extend through said block from a position above said upper bite surface to a position below said lower bite surface and a film-locking slot extending substantially horizontally through said bite portion between said upper bite surface and said lower bite surface and in communication with said film-holding slot;
   a bite block holder means including a film-locking portion at one end thereof, said film-locking portion adapted to be removably received by said film-locking slot, said film-locking portion adapted to engage the film and hold the film in one of a plurality of fixed positions extending above and/or below said upper and lower bite surface respectively; and
   x-ray beam alignment means coupled to said bite block holder means for assisting in the alignment of an x-ray beam with the film in said film-holding slot.

2. The apparatus of claim 1 wherein said bite portion is sufficiently flexible so as to clamp said film locking slot closed on said film-locking portion in response to pressure of the teeth on said upper bite surface and said lower bite surface.

3. The apparatus of claim 1 wherein said locking portion comprises a roughened surface adapted to engage the film in the area of communication between said film-holding slot and said film-locking slot.

4. The apparatus of claim 3 wherein said film-locking portion is tapered and said film-locking slot is tapered in a similar manner such that said film-locking portion is wedged against the film.

5. The apparatus of claim 4 wherein said film-holding slot includes a depression opposite said film-locking slot such that said film may be forced into said depression by said film-locking portion to assist in locking said film in place.

6. The apparatus of claim 1 wherein said x-ray beam alignment means comprises positioning means including indicia for indicating mandibular periapical, bite-wing and maxillary periapical positions of alignment for the x-ray beam.

7. The apparatus of claim 6 wherein said positioning means is color coded for said mandibular periapical, said bite-wing and said maxillary periapical positions.

8. The apparatus of claim 1 wherein said x-ray beam alignment means comprises a substantially planar piece of radio transparent material.

9. The apparatus of claim 1 further comprising means for generating an x-ray beam of circular cross-section.

10. The apparatus of claim 1 further comprising means for generating an x-ray beam of rectangular cross-section.

11. The apparatus of claim 10 wherein said means for generating an x-ray beam of rectangular cross-section comprises a radio opaque tube or circular cross-section and a removable radio opaque cap having a rectangular orifice.

12. The apparatus of claim 11 wherein said beam alignment means further comprises rectangular positioning means for indicating a position of horizontal alignment as well as vertical alignment for said rectangular orifice for mandibular periapical, bite-wing and maxillary periapical positions of the film.

13. The apparatus of claim 12 wherein said radio opaque cap includes projections extending radially outwardly beyond the circular tube, said projections being aligned with said indicia on said beam alignment means.

14. The apparatus of claim 13 wherein said projections at least partially form a generally rectangular outline and said indicia on said beam alignment means least partially form a rectangular outline.

15. The apparatus of claim 14 further comprising additional beam alignment means for aligning a beam of circular cross-section with said film, said rectangular beam alignment means being removably attached to said additional beam alignment means.

16. The apparatus of claim 1 wherein said upper bite surface includes a line intersecting the center of said film-holding slot and said film at the center thereof to assist in locating the film.

17. The apparatus of claim 1 in combination with an occlusal film support means comprising a coupling portion adapted to be received by said film-holding slot and a film backing portion adapted to support said film, said film backing portion forming an obtuse angle with said upper surface so as to support said film in the occlusal position.

18. The apparatus of claim 17 wherein said obtuse angle is in the range of 105°–135°.

19. The apparatus of claim 18 wherein said obtuse angle is substantially 120°.

20. The apparatus of claim 1 wherein said film support means comprises a coupling portion adapted to be received by said film-holding slot and a film backing portion adapted to support said film, said coupling portion forming an obtuse angle with said film backing portion so as to support said film in the occlusal position.

21. The apparatus of claim 20 wherein said obtuse angle is in the range of 135°–165°.

22. The apparatus of claim 21 wherein said obtuse angle is substantially 150°.

23. The apparatus of claim 20 wherein said film support means comprises a groove for receiving film.

24. The apparatus of claim 20 wherein said beam alignment means comprises a substantially planar surface adapted to extend substantially transverse to the beam, said substantially planar surface forming an angle in the range of 15°–45° with said film backing portion.

25. The apparatus of claim 24 wherein said angle of said planar surface with said film backing portion is substantially 30°.

26. The apparatus of claim 20 wherein said film support means comprises a groove forming portion extending along said backing portion generally away from said coupling portion so as to form a groove with said backing portion for receiving film.

27. Apparatus for positioning dental x-ray film within the mouth comprising:
film support means;
a block having a first longitudinally extending surface and a second longitudinally extending surface, a first slot extending through said block in a direction generally transverse to said first and second longitudinally extending surfaces so as to permit said film support means to be inserted into said first slot from one side adjacent said first longitudinally extending surface, said block including a second slot extending generally parallel and between said first longitudinally extending surface and said second longitudinally extending surface, said second slot being in direct communication with said first slot;
block holder means including a locking portion at one end thereof, said locking portion adapted to be removably received by said second slot, said locking portion also adapted to apply pressure to said film support means and hold said film support means in place when said film support means is inserted into said first slot; and
x-ray beam alignment means coupled to said bite block holder means for assisting in the alignment of an x-ray beam with x-ray film supported by said film support means.

28. The apparatus of claim 17 wherein said film support means comprises a substantially planar member.

29. The apparatus of claim 27 wherein said film support means comprises a coupling portion adapted to be received by said first slot and a film backing portion adapted to support said film, said film backing portion forming an obtuse angle with said first longitudinally extending surface so as to support said film in the occlusal position.

30. The apparatus of claim 29 wherein said obtuse angle lies in the range of 105°-135°.

31. The apparatus of claim 30 wherein said obtuse angle is substantially 120°.

32. The apparatus of claim 27 wherein said film support means comprises a coupling portion adapted to be received by said first slot and a film-backing portion adapted to support said film, said coupling portion forming an obtuse angle with said film backing portion so as to support said film in the occlusal position.

33. The apparatus of claim 32 wherein said obtuse angle lies in the range of 135°-165°.

34. The apparatus of claim 32 wherein said obtuse angle is substantially 120°.

35. The apparatus of claim 34 wherein said film support means comprises a groove for receiving film.

36. The apparatus of claim 27 wherein said beam alignment means comprises a substantially planar surface adapted to extend substantially transverse to the x-ray beam.

37. Apparatus for positioning x-ray film in the occlusal position within the mouth comprising:
a film holder including a substantially planar combination film backing bite portion for supporting film in the occlusal position between teeth; and
x-ray beam alignment means attached to said film holder, said x-ray beam alignment means being adapted to assist in maintaining an angle of 105°-135° between said film backing-bite portion and the axis of the x-ray beam.

38. The apparatus of claim 37 wherein said angle is substantially 120°.

39. The apparatus of claim 37 wherein a portion of said x-ray beam alignment means extends in a plane parallel to said axis.

40. The apparatus of claim 37 wherein said film holder comprises a coupling portion forming an angle of substantially 135°-165° with respect to said film backing-bite portion.

41. The apparatus of claim 40 wherein said x-ray beam alignment means comprises a bite block having a film-holding slot adapted to receive film for practicing a right angle technique, said slot also being adapted to receive said coupling portion.

42. The apparatus of claim 37 further comprising a groove adjacent said film backing-bite portion at one end thereof.

43. Apparatus for positioning dental x-ray film within the mouth comprising:
a block having a first slot and a second slot intersecting with said first slot, said first slot adapted to receive film,
a block holder means including a locking portion at one end thereof, said locking portion adapted to be removably received by said second slot, said locking portion also adapted to apply pressure to said film when said film is inserted in said second slot; and
x-ray beam alignment means coupled to said bite block holder means for assisting in the alignment of an x-ray beam.

44. Apparatus for positioning dental x-ray film within the mouth comprising:
a block having a first slot and a second slot intersecting with said first slot, said first slot adapted to receive film support means;
a block holder means including a locking portion at one end thereof, said locking portion adapted to be removably received by said second slot, said locking portion also adapted to apply pressure to said film support means and hold said film support means in place when said film support means is inserted into said second slot; and
x-ray beam alignment means coupled to said block holder means for assisting in the alignment of an x-ray beam.

* * * * *

UNITED STATES PATENT AND TRADEMARK OFFICE
CERTIFICATE OF CORRECTION

PATENT NO. : 4,048,506

DATED : September 13, 1977

INVENTOR(S) : William J. Updegrave

It is certified that error appears in the above-identified patent and that said Letters Patent are hereby corrected as shown below:

Column 2, line 35, delete "in" and insert --on--.

Signed and Sealed this

Thirteenth Day of June 1978

[SEAL]

Attest:

RUTH C. MASON
Attesting Officer

DONALD W. BANNER
Commissioner of Patents and Trademarks